(12) United States Patent
Yoshinaga et al.

(10) Patent No.: US 11,452,434 B2
(45) Date of Patent: Sep. 27, 2022

(54) MEDICAL DEVICE AND ENDOSCOPE SYSTEM

(71) Applicant: OLYMPUS CORPORATION, Tokyo (JP)

(72) Inventors: Takuto Yoshinaga, Hachioji (JP); Chikayoshi Meguro, Hachioji (JP); Tatsuhiko Suzuki, Kunitachi (JP)

(73) Assignee: OLYMPUS CORPORATION, Tokyo (JP)

( * ) Notice: Subject to any disclaimer, the term of this patent is extended or adjusted under 35 U.S.C. 154(b) by 280 days.

(21) Appl. No.: 16/822,316

(22) Filed: Mar. 18, 2020

(65) Prior Publication Data

US 2020/0214542 A1    Jul. 9, 2020

Related U.S. Application Data

(63) Continuation of application No. PCT/JP2018/029673, filed on Aug. 7, 2018.

(30) Foreign Application Priority Data

Oct. 31, 2017  (JP) .............................. JP2017-210229

(51) Int. Cl.
    *A61B 1/00*      (2006.01)
    *A61B 1/005*     (2006.01)
    *A61B 1/012*     (2006.01)

(52) U.S. Cl.
    CPC ........ *A61B 1/0052* (2013.01); *A61B 1/00002* (2013.01); *A61B 1/00133* (2013.01); *A61B 1/0125* (2013.01)

(58) Field of Classification Search
    None
    See application file for complete search history.

(56) References Cited

U.S. PATENT DOCUMENTS 3,610,231 A *  10/1971  Takahashi ............ A61B 1/0057
                                                         396/17
5,413,107 A     5/1995  Oakley et al.
(Continued)

FOREIGN PATENT DOCUMENTS

EP          2 005 874 A1    12/2008
JP         2009-530051 A     8/2009
(Continued)

OTHER PUBLICATIONS

International Search Report dated Sep. 18, 2018 received in PCT/JP2018/029673.

*Primary Examiner* — Timothy J Neal
(74) *Attorney, Agent, or Firm* — Scully, Scott, Murphy & Presser, P.C.

(57) ABSTRACT

A baby endoscope which forms a medical device includes: a rotary member; an exterior member which rotatably holds the rotary member about a predetermined rotation axis, houses the rotary member in the exterior member, and has a surface which is brought into contact with a portion of an outer peripheral surface of an operation section of a mother endoscope on an outer peripheral portion; and a bending operation lever mounted on the rotary member, and is disposed within a width of the exterior member in a direction of the rotation axis when the exterior member is viewed in a direction orthogonal to the rotation axis.

14 Claims, 8 Drawing Sheets

(56) References Cited

U.S. PATENT DOCUMENTS

| | | | |
|---|---|---|---|
| 2005/0272975 A1* | 12/2005 | McWeeney | A61B 6/06 600/172 |
| 2013/0303855 A1* | 11/2013 | Masaki | A61B 1/0016 600/146 |
| 2017/0325660 A1* | 11/2017 | Wang | A61B 1/00066 |

FOREIGN PATENT DOCUMENTS

| | | |
|---|---|---|
| WO | 95/22284 A1 | 8/1995 |
| WO | 2005/094665 A2 | 10/2005 |

* cited by examiner

MEDICAL DEVICE AND ENDOSCOPE SYSTEM

CROSS REFERENCE TO RELATED APPLICATION

This application is a continuation application of PCT/JP2018/029673 filed on Aug. 7, 2018 and claims benefit of Japanese Application No. 2017-210229 filed in Japan on Oct. 31, 2017, the entire contents of which are incorporated herein by this reference.

BACKGROUND OF INVENTION

1. Field of the Invention

The present invention relates to a medical device, and more particularly to a medical device which is mountable on an operation section of an endoscope.

2. Description of the Related Art

Conventionally, a medical device which is used with an endoscope and observes or treats the inside of a subject has been put into practice or has been proposed.

For example, a mother-baby endoscope which is formed of: a mother endoscope; and a baby endoscope, an insertion section of which is insertable into a treatment instrument insertion channel of the mother endoscope, has been put into practice. Alternatively, for example, Japanese Patent Application Laid-Open Publication No. 2009-530051 discloses a medical system which is formed of: an endoscope; and a catheter assembly which is insertable into a biopsy port of the endoscope.

A surgeon can observe or treat, for example, the inside of a bile duct or the inside of a pancreatic duct of the subject using two devices formed of a mother endoscope and a baby endoscope or two devices formed of an endoscope and a medical device.

Usually, the surgeon performs an insertion operation by gripping the insertion section of the endoscope with his right hand, and performs various operations of the endoscope by gripping the operation section of the endoscope with his left hand. Accordingly, in the case of the mother-baby endoscope, it is not possible for the surgeon to operate both the mother endoscope and the baby endoscope by himself alone. Similarly, it is not possible either for the surgeon to operate both the endoscope and the catheter assembly by himself alone.

SUMMARY OF THE INVENTION

According to an aspect of the present invention, there is provided a medical device to be fixed to an operation section of an endoscope, the medical device includes: an insertion section configured to be inserted into a treatment instrument insertion opening of the endoscope, and having a bending portion which is bendable; a housing disposed on a proximal end side of the insertion section, and having a first surface which is attached to a grasping portion of the endoscope; and an operation member rotatably mounted on the housing about a first rotation axis, the operation member being configured to bend the bending portion, wherein the first surface is formed such that the first rotation axis and a second rotation axis of a rotary member mounted on the operation section of the endoscope become parallel to each other or become substantially parallel to each other when the housing is mounted on the grasping portion of the endoscope, and the operation member is disposed on a second surface which makes an approximately 90 degrees with respect to the first surface and is parallel to a longitudinal axis of the housing, and the operation member is disposed within a width of the housing in a direction of the first rotation axis when the housing is viewed in a direction orthogonal to the first rotation axis.

According to another aspect of the present invention, there is provided a medical device to be fixed to an operation section of an endoscope, the medical device includes: an insertion section configured to be inserted into a treatment instrument insertion opening of the endoscope, and having a bending portion which is bendable; a housing disposed on a proximal end side of the insertion section, and having a surface which is attached to a grasping portion of the endoscope; a fixing member configured to fix the housing to the operation section of the endoscope; and an operation member rotatably mounted on the housing about a first rotation axis, the operation member being configured to bend the bending portion, wherein the surface includes a planar surface portion being flat or approximately flat, the planar surface portion being formed such that the first rotation axis and a second rotation axis of a rotary member mounted on the operation section of the endoscope become parallel to each other or become substantially parallel to each other when the housing is mounted on the grasping portion of the endoscope, and the operation member is disposed within a width of the housing in a direction of the first rotation axis when the housing is viewed in a direction orthogonal to the first rotation axis.

According to another aspect of the present invention, there is provided an endoscope system which includes: an endoscope; and a medical device fixed to an operation section of the endoscope, wherein the medical device includes: an insertion section inserted into a treatment instrument insertion opening of the endoscope, and having a bending portion which is bendable; a housing disposed on a proximal end side of the insertion section, and having a first surface which is attached to a grasping portion of the endoscope; and an operation member rotatably mounted on the housing about a first rotation axis, the operation member being configured to bend the bending portion, and the first surface is formed such that the first rotation axis and a second rotation axis of a rotary member mounted on the operation section of the endoscope become parallel to each other or become substantially parallel to each other when the housing is mounted on the grasping portion of the endoscope, and the operation member is disposed on a second surface which makes an approximately 90 degrees with respect to the first surface and is parallel to a longitudinal axis of the housing, and the operation member is disposed within a width of the housing in a direction of the first rotation axis when the housing is viewed in a direction orthogonal to the first rotation axis.

According to another aspect of the present invention, there is provided an endoscope system which includes: an endoscope; and a medical device fixed to an operation section of the endoscope, wherein the medical device includes: an insertion section inserted into a treatment instrument insertion opening of the endoscope, and having a bending portion which is bendable; a housing disposed on a proximal end side of the insertion section, and having a surface which is attached to a grasping portion of the endoscope; a fixing member configured to fix the housing to the operation section of the endoscope; and an operation member rotatably mounted on the housing about a first rotation axis, the operation member being configured to bend the bending portion, and the surface includes a planar surface portion being flat or approximately flat, the planar surface portion being formed such that the first rotation axis and a second rotation axis of a rotary member mounted on the operation section of the endoscope become parallel to each other or become substantially parallel to each other when the housing is mounted on the grasping portion of the endoscope, and the operation member is disposed within a width of the housing in a direction of the first rotation axis when the housing is viewed in a direction orthogonal to the first rotation axis.

DETAILED DESCRIPTION OF THE PREFERRED EMBODIMENT(S)

Hereinafter, an embodiment of the present invention is described with reference to drawings.

Figure 1:
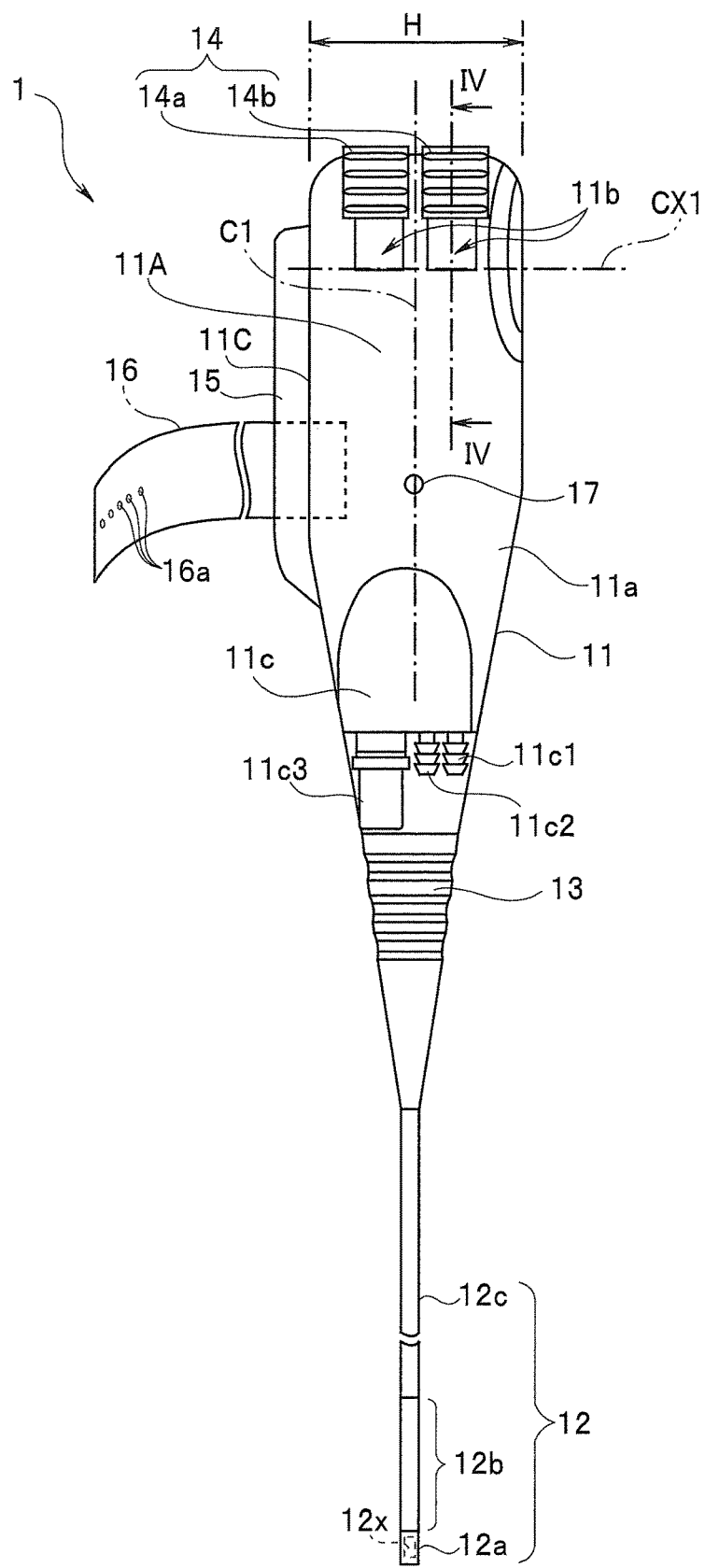
FIG. 1 is a front view of a baby endoscope according to an embodiment of the present invention.
Figure 2:
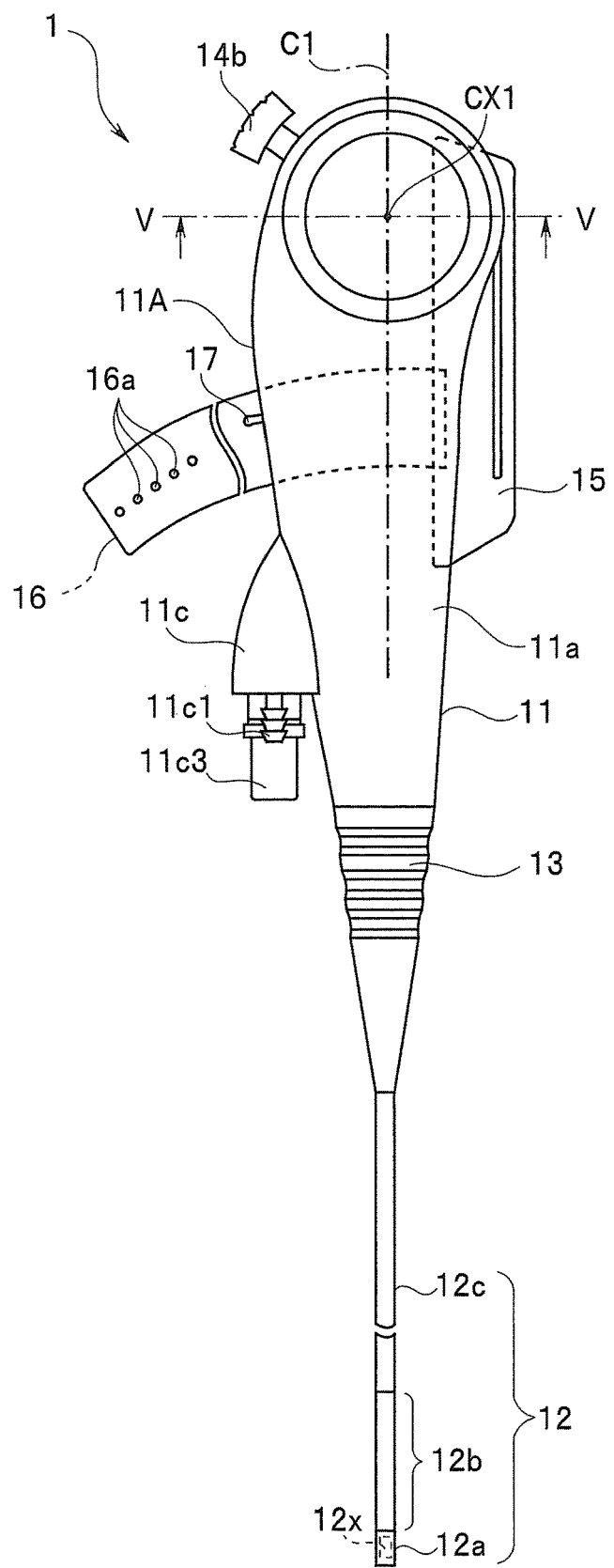
FIG. 2 is a right side view of the baby endoscope according to the embodiment of the present invention.
Figure 3:
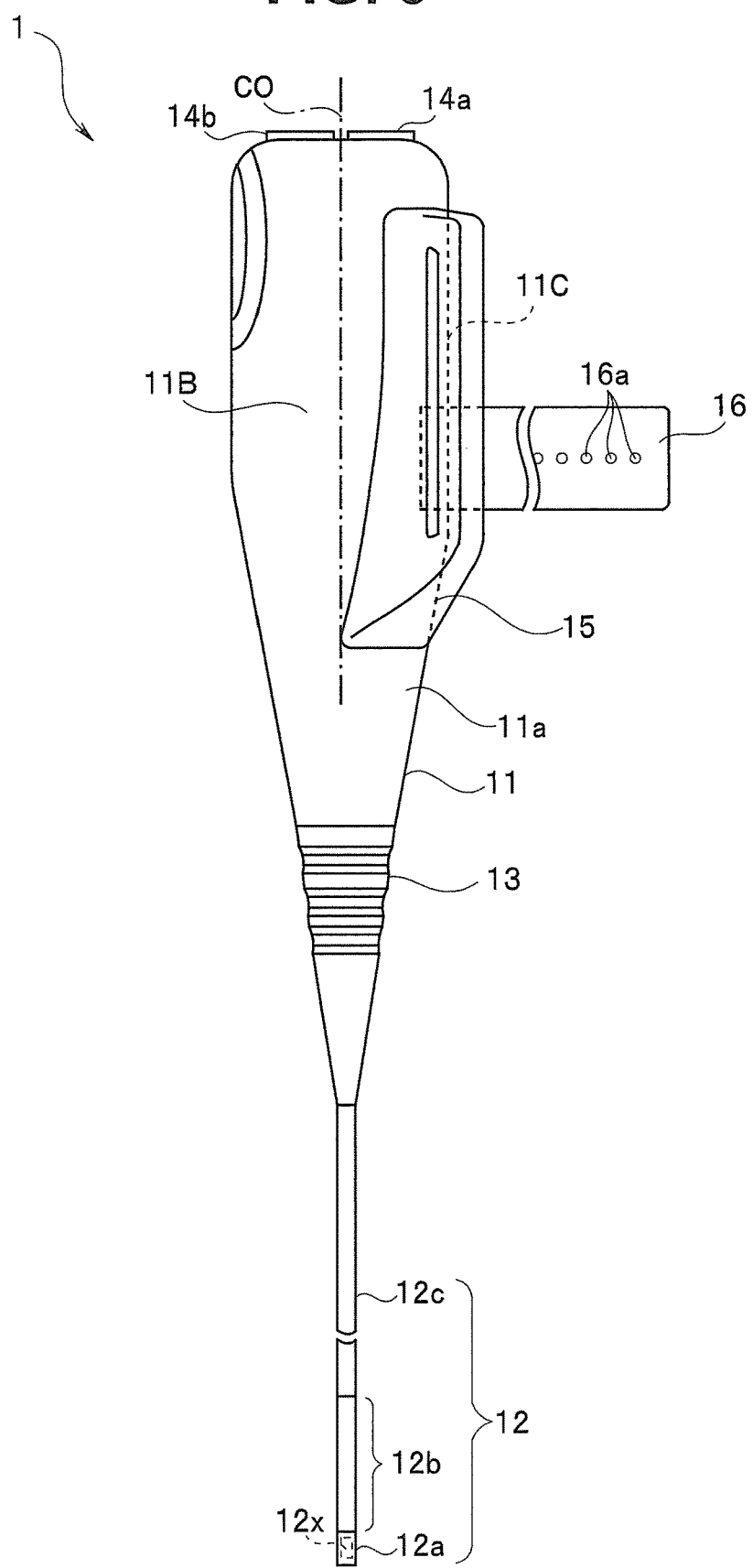
FIG. 3 is a back view of the baby endoscope according to the embodiment of the present invention.

FIG. 1 is a front view of a baby endoscope according to the embodiment. FIG. 2 is a right side view of the baby endoscope according to the embodiment. FIG. 3 is a back view of the baby endoscope according to the embodiment.

The baby endoscope 1 according to the embodiment includes an operation section 11 and an insertion section 12. The baby endoscope 1 is a medical device which is used with a mother endoscope 2 described later in a state where the insertion section 12 is inserted into a treatment instrument insertion opening of the mother endoscope 2. The baby endoscope 1 is an endoscope separate from the mother endoscope 2.

The insertion section 12 includes a distal end portion 12a, a bending portion 12b, and a flexible tube portion 12c arranged in this order from a distal end side of the insertion section 12. A proximal end portion of the flexible tube portion 12c is connected to a distal end of the operation section 11 by way of a bend preventing portion 13 formed on the operation section 11. With such a configuration, the elongated insertion section 12 extends in a direction of the distal end of operation section 11 from an exterior member 11a of the operation section 11 which forms a housing by way of the bend preventing portion 13.

An outer diameter of the insertion section 12 is smaller than an inner diameter of a treatment instrument insertion channel of the mother endoscope 2, and has a size and a shape which allow the insertion of the insertion section 12 to pass through the treatment instrument insertion channel of the mother endoscope 2.

An observation window and an illumination window not shown in the drawings are mounted on a distal end surface of the distal end portion 12a of the insertion section 12. Openings for suction and air/water feeding (not shown in the drawings) are also formed on the distal end surface of the distal end portion 12a.

An image pickup unit 12x which includes an image pickup device and an objective optical system is incorporated in the distal end portion 12a. The image pickup unit 12x generates an image pickup signal of an image of the inside of a subject which receives light through the observation window, and outputs the image pickup signal. A drive signal for driving the image pickup device and an image pickup signal from the image pickup device are transmitted via a signal cable (not shown in the drawings) which passes through the insertion section 12.

On a back surface of the illumination window, a distal end surface of a light guide (not shown in the drawings) which passes through the insertion section 12 is disposed. An illumination light emitted from the distal end surface of the light guide is radiated to the subject through the illumination window. The light guide is formed of a bundle of optical fibers for illumination.

The openings formed in the distal end surface of the distal end portion 12a are connected with a suction channel and a water feeding channel not shown in the drawing which pass through the insertion section 12.

The operation section 11 has an approximately rectangular parallelepiped shape. The insertion section 12 extends from the operation section 11 in a first direction along a longitudinal axis C1 of the operation section 11 (a downward direction in FIG. 1, FIG. 2, and FIG. 3).

A portion of the operation section 11 on a distal end side has a gradually narrowed tapered shape, and the bend preventing portion 13 has a shape which is continuously formed along the tapered shape of the operation section 11. The exterior member 11a of the operation section 11 is made of a resin such as polycarbonate.

The operation section 11 has a bending operation portion 14 on a portion on a second direction side (upper side in FIG. 1 and FIG. 2) which is a side opposite to the first direction side along the longitudinal axis C1 of the operation section 11.

The bending operation portion 14 has two bending operation members for performing a bending operation of the bending portion 12b. One of two bending operation members is a bending operation lever 14a for bending the bending portion 12b in a vertical direction, and the other bending operation member is a bending operation lever 14b for bending the bending portion 12b in a lateral direction.

In this embodiment, the vertical direction substantially agrees with a vertical direction of an endoscope image obtained by picking up by the pickup unit 12x of the baby endoscope 1 and displayed on an endoscope image monitor not shown in the drawings. The lateral direction substantially agrees with a lateral direction of the endoscope image displayed on the endoscope image monitor.

The respective bending operation levers 14a, 14b are configured to be rotatable within a predetermined angular range about a rotation axis CX1 orthogonal to the longitudinal axis C1 of the operation section 11. Accordingly, in the exterior member 11a of the operation section 11, two narrow elongated openings 11b are formed parallel to each other along the rotation of two bending operation levers 14a, 14b.

Accordingly, the respective bending operation levers 14a, 14b are movable from a surface 11A of the operation section 11 on a front side toward a proximal end side (an upper side in FIG. 1) of the operation section 11.

The rotary mechanisms of the respective bending operation levers 14a, 14b are described later.

A finger touching portion 15 is formed in the operation section 11. The finger touching portion 15 may be fixed to the operation section 11 by a screw or the like, or may be integrally formed with the exterior member 11a of the operation section 11.

The finger touching portion 15 is formed on a surface 11B of the operation section 11 on a side opposite to a surface 11A of the operation section 11 in a state where the finger touching portion 15 protrudes toward the outside. The finger touching portion 15 extends long along the longitudinal axis C1 of the operation section 11, and is formed such that a middle finger of a left hand of a surgeon can be easily caught by the finger touching portion 15 as described later.

A belt 16 for fixing which is made of a resin material having flexibility and stretching property such as elastomer extends from a portion in the vicinity of the finger touching portion 15. The belt 16 is a fixing member for fixing the baby endoscope 1 to the mother endoscope 2 having an operation section 101.

A plurality of holes 16a are formed on a distal end side of the belt 16 along a longitudinal axis of the belt 16. A proximal end portion of the belt 16 is fixed to the exterior member 11a in the vicinity of the finger touching portion 15 by a screw, an adhesive agent or the like.

On the surface 11A of the exterior member 11a of the operation section 11 disposed on a side opposite to the surface 11B on which the finger touching portion 15 is formed, a pin 17 which can pass through one of the plurality of holes 16a is disposed. The pin 17 may be integrally formed with the exterior member 11a, or may be fixedly mounted on the exterior member 11a by a screw or the like as a separate member.

The plurality of holes 16a are formed in the belt 16 such that the baby endoscope 1 can be mounted and fixed to the mother endoscope 2 corresponding to various sizes of the operation sections of the mother endoscopes 2.

In this embodiment, the belt 16 is used as a fixing member. However, a magnet, an adhesive tape, a C-shaped hook member or the like may be used as the fixing member.

Accordingly, with respect to the longitudinal axis C1, a surface 11C of the operation section 11 on the mother endoscope 2 has a flat or an approximately flat planar surface portion which oppositely faces a side surface of the operation section 101 of the mother endoscope 2.

A connecting portion 11c for connection with an external equipment is formed on the operation section 11. The connecting portion 11c has a shape where a portion of the exterior member 11a protrudes. The connecting portion 11c includes: a pipe sleeve 11c1 to which an air/water feeding tube (not shown in the drawings) is connected; a pipe sleeve 11c2 to which a suction tube (not shown in the drawings) is connected; and a connector 11c3 to which a composite cable (not shown in the drawings) through which a light guide and an image pickup cable pass together is connected.

In this embodiment, the composite cable or the like not shown in the drawings is connected to the connector 11c3 or the like of the connecting portion 11c. However, the air/water feeding tube, the suction tube, the composite cable, and the operation section 11c may be integrally formed with each other, and the air/water feeding tube, the suction tube, and the composite cable may extend from the operation section 11c.

The pipe sleeves 11c1, 11c2, and the connector 11c3 are arranged in a protruding manner in an extending direction (that is, a distal end direction) of the insertion section 12 along the longitudinal axis C1 of the operation section 11.

Next, the structure of the operation section 11 of the baby endoscope 1 is described.

Figure 4:
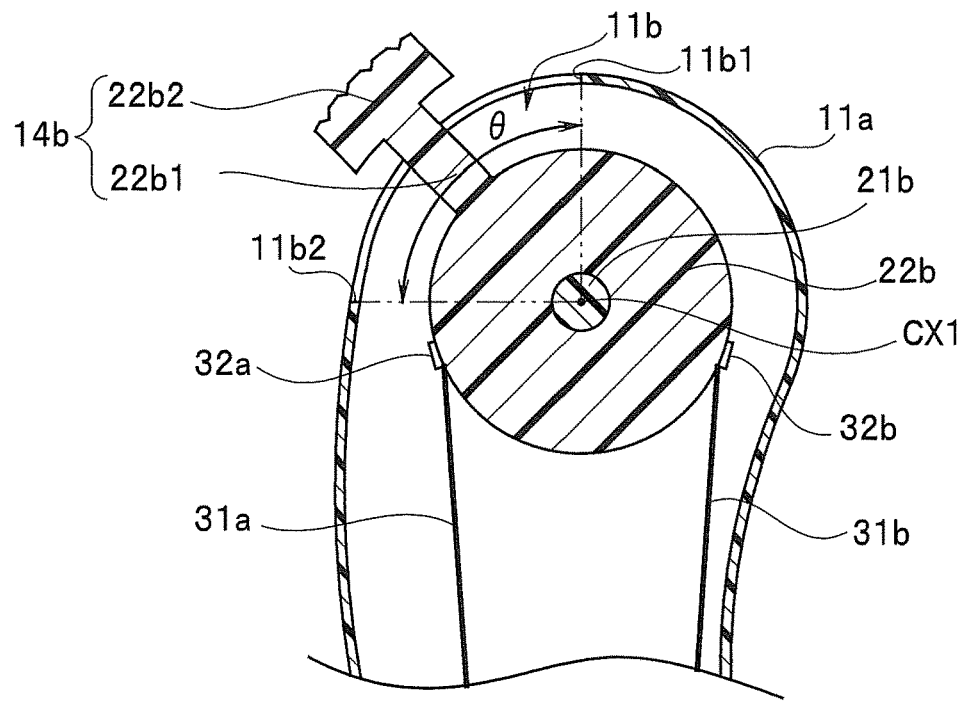
FIG. 4 is a cross-sectional view of an operation section 11 of the baby endoscope 1 taken along line IV-IV in FIG. 1.
Figure 5:
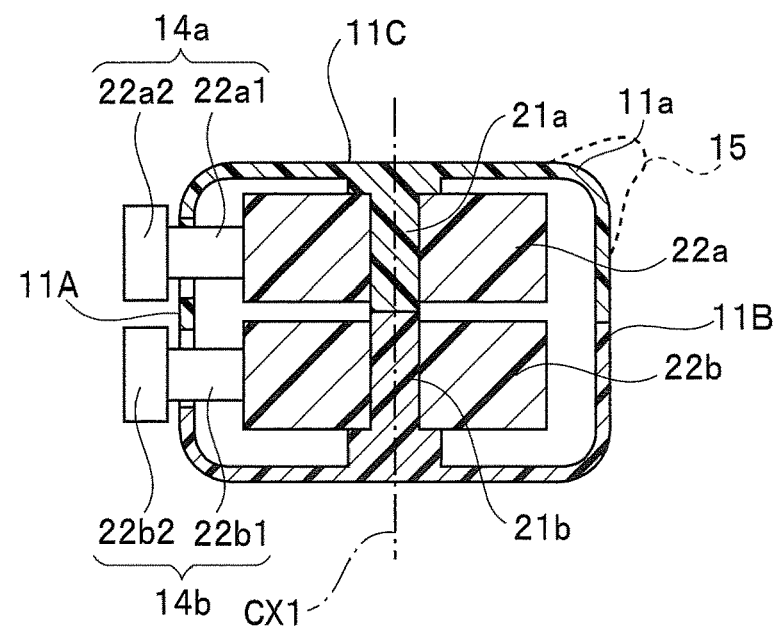
FIG. 5 is a cross-sectional view of the operation section 11 of the baby endoscope 1 taken along line V-V in FIG. 2.

FIG. 4 is a cross-sectional view of the operation section 11 of the baby endoscope 1 taken along line IV-IV in FIG. 1. FIG. 5 is a cross-sectional view of the operation section 11 of the baby endoscope 1 taken along line V-V in FIG. 2.

As shown in FIG. 5, two circular columnar portions 21a, 21b which protrude in the operation section 11 along the rotation axis CX1 are disposed in the exterior member 11a of the operation section 11. As described above, the rotation axis CX1 is orthogonal to the longitudinal axis C1 of the operation section 11 and hence, two circular columnar portions 21a, 21b are also formed orthogonal to the longitudinal axis C1 of the operation section 11.

Two rotary members 22a, 22b are disposed in the operation section 11.

The rotary member 22a has a circular plate shape, and the circular columnar portion 21a is allowed to pass through a hole formed at a center of a circular shape, and the rotary member 22a is rotatably mounted on the operation section 11 about the rotation axis CX1.

Similarly, the rotary member 22b also has a circular plate shape, and the circular columnar portion 21b is allowed to pass through a hole formed at a center of a circular shape, and the rotary member 22b is rotatably mounted on the operation section 11 about the rotation axis CX1.

As described above, the exterior member 11a which forms a housing rotatably supports the rotary members 22a, 22b about the predetermined rotation axis CX1, and houses the rotary members 22a, 22b in the exterior member 11a.

The rotary member 22a has an extending portion 22a1 which extends in a radially outer direction, and an operation contact portion 22a2 is formed on a distal end portion of the extending portion 22a1. The extending portion 22a1 and the operation contact portion 22a2 form the bending operation lever 14a.

Similarly, the rotary member 22b has an extending portion 22b1 which extends in a radially outer direction, and an operation contact portion 22b2 is formed on a distal end portion of the extending portion 22b1. The extending portion 22b1 and the operation contact portion 22b2 form the bending operation lever 14b.

As described above, the bending operation levers 14a, 14b which form the operation members are formed in an extending manner from two rotary members 22a, 22b.

Although not shown in the drawings, the exterior member 11a is formed of two members obtained by splitting the exterior member 11a in two along a plane parallel to the longitudinal axis C1 and parallel to the surface 11C. The operation section 11 is formed by fixing two members to each other by an adhesive agent or the like.

Although two bending operation levers 14a, 14b are rotatable about the rotation axis CX1, a rotation range of two bending operation levers 14a, 14b are restricted by end portions of two narrow elongated openings 11b formed on the exterior member 11a.

In this embodiment, the rotation range of the respective bending operation levers 14a, 14b is restricted as the extending portions 22a1, 22b1 of the respective bending operation levers 14a, 14b are brought into contact with upper side end portions 11b1 and lower side end portions 11b2 of the respective openings 11b.

The rotation range of two bending operation levers 14a, 14b may be restricted by projecting portions or the like formed in the exterior member 11a and restricting portions such as projecting portions formed on or mounted on the rotary members 22a, 22b.

The respective bending operation levers 14a, 14b are movable within a range from a position on the surface 11A of the operation section 11 to a position on a surface of the operation section 11 on a proximal end side. Accordingly, the respective bending operation levers 14a, 14b are rotatable only within a range of an angle θ indicated in FIG. 4.

As shown in FIG. 4, respective one ends of two bending wires 31a, 31b for lateral bending are fixed to an outer peripheral portion of the rotary member 22b by fixing members such as screws 32a, 32b.

Similarly, respective one ends of two bending wires (not shown in the drawings) for vertical bending are fixed to an outer peripheral portion of the rotary member 22a by fixing members such as screws.

Accordingly, a surgeon can bend the bending portion 12b in the vertical direction by towing and relaxing two bending wires by operating the bending operation lever 14a. Further, the surgeon can bend the bending portion 12b in the lateral direction by towing and relaxing two bending wires 31a, 31b by operating the bending operation lever 14b.

As described above, the baby endoscope 1 has two wires, one end of each of which is fixed to the respective rotary members 22a, 22b in the exterior member 11a. The bending portion 12b which is formed on the insertion section 12 and includes a plurality of bending pieces is bendable by towing and relaxing of four wires, the other end of each of which is fixed to one of the plurality of bending pieces.

Next, a state where the baby endoscope 1 is mounted on the mother endoscope 2 and the operation of the baby endoscope 1 are described.

Figure 6:
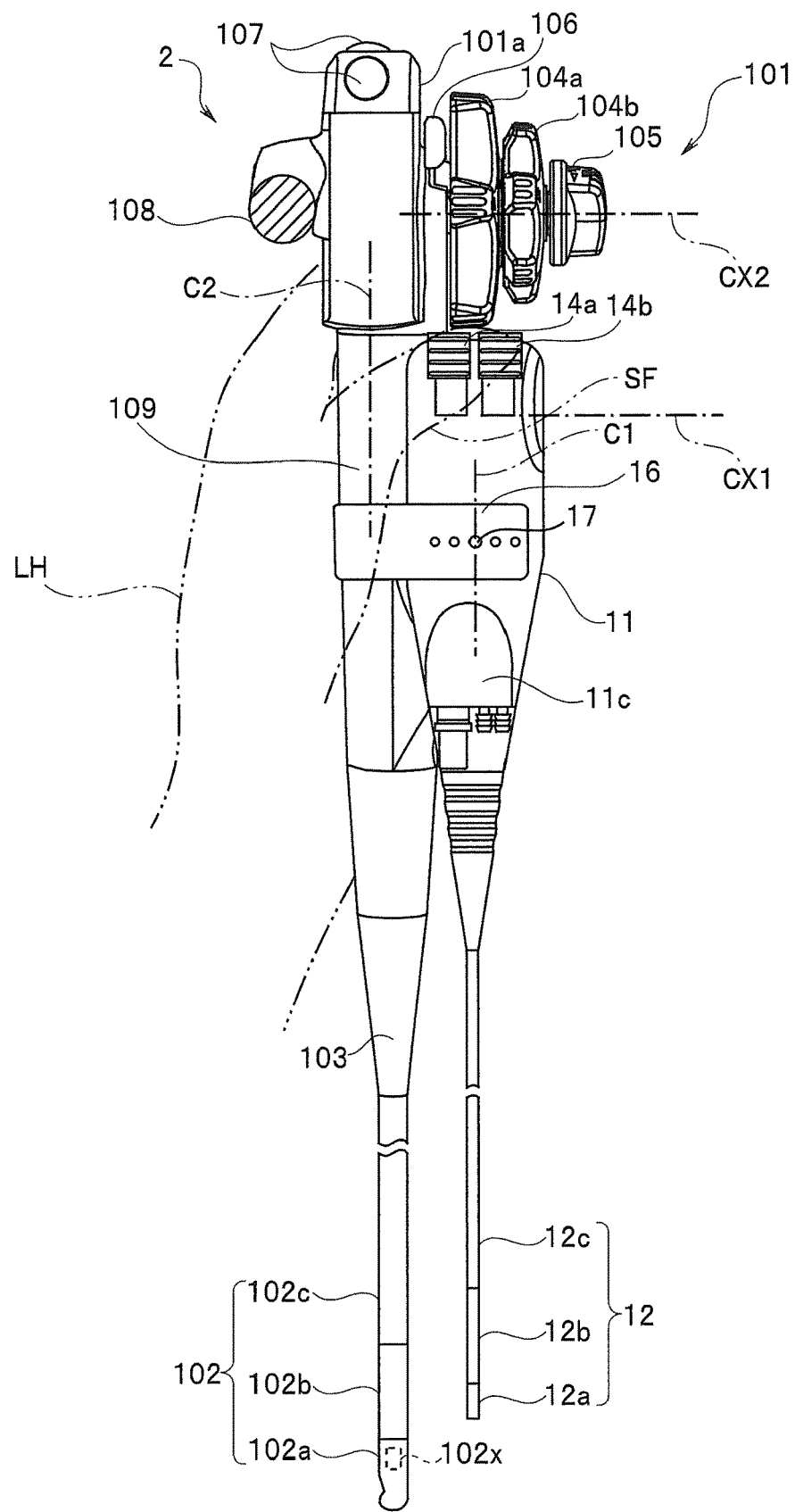
FIG. 6 is a front view of the baby endoscope fixed to a mother endoscope according to the embodiment of the present invention.
Figure 7:
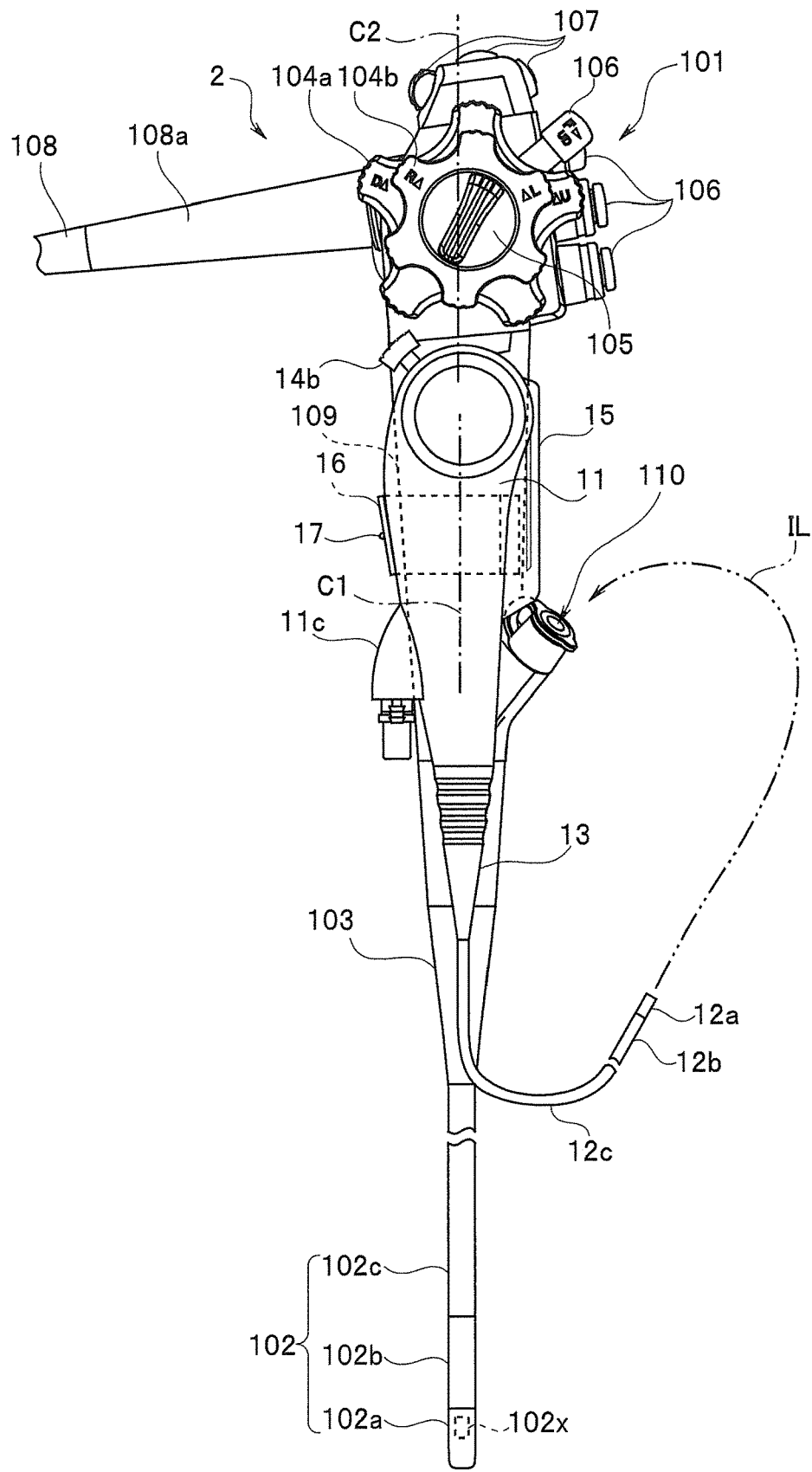
FIG. 7 is a side view of the baby endoscope fixed to the mother endoscope according to the embodiment of the present invention.

FIG. 6 is a front view of the baby endoscope fixed to the mother endoscope according to the embodiment. FIG. 7 is a side view of the baby endoscope fixed to the mother endoscope according to the embodiment.

Firstly, the configuration of the mother endoscope 2 is described.

The mother endoscope 2 has an operation section 101 and an insertion section 102. The insertion section 102 includes a distal end portion 102a, a bending portion 102b, and a flexible tube portion 102c arranged in this order from a distal end side of the insertion section 102. A proximal end portion of the flexible tube portion 102c is connected to a distal end of the operation section 101 by way of a bend preventing portion 103 formed on the operation section 101.

The mother endoscope 2 is a side viewing endoscope, and an observation window and an illumination window not shown in the drawings are mounted on the distal end portion 102a.

Accordingly, an image pickup unit 102x which includes an image pickup device and an objective optical system is incorporated in the distal end portion 102a. The image pickup unit 102x generates an image pickup signal of an image of the inside of a subject which receives light through the observation window, and outputs the image pickup signal. A drive signal for driving the image pickup device and an image pickup signal from the image pickup device are transmitted via a signal cable (not shown in the drawings) which passes through the insertion section 102.

On a back surface of the illumination window, a distal end surface of a light guide (not shown in the drawings) which passes through the insertion section 102 is disposed. An illumination light emitted from the distal end surface of the light guide is radiated to the subject through the illumination window.

A treatment instrument insertion channel (not shown in the drawings) is formed in the insertion section 102, and the insertion section 12 of the baby endoscope 1 is allowed to pass through the treatment instrument insertion channel.

Further, in the distal end portion 102a, a treatment instrument raising platform (not shown in the drawings) is disposed. The treatment instrument raising platform is provided for raising the insertion section 12 of the baby endoscope 1 which is allowed to pass through the treatment instrument insertion channel and protrudes from an opening formed in the distal end portion 102a.

The operation section 101 has an approximately rectangular parallelepiped shape. The insertion section 102 extends from the operation section 101 in a first direction along a longitudinal axis C2 of the operation section 101 (a downward direction in FIG. 6 and FIG. 7). A portion of the operation section 101 on a first direction side has a gradually narrowed tapered shape, and the bend preventing portion 103 has a shape which is continuously formed along the tapered shape of the operation section 101. An exterior member 101a of the operation section 101 is made of a resin such as modified polyphenyl ether.

Two bending operation knobs 104a, 104b are mounted on the operation section 101. These bending operation knobs 104a, 104b are rotatable about a rotation axis CX2 which is orthogonal to the longitudinal axis C2 of the operation section 101 and protrudes from the exterior member 101a of the operation section 101. The bending operation knob 104a disposed near the exterior member 101a is a bending operation member provided for bending the bending portion 102b in a vertical direction, and the bending operation knob 104b disposed remote from the exterior member 101a is a bending operation member provided for bending the bending portion 102b in a lateral direction.

In this embodiment, the vertical direction agrees with a vertical direction of an endoscope image obtained by picking up an image by an image pickup unit 102x of the mother endoscope 2 and displayed on an endoscope image monitor not shown in the drawings. The lateral direction agrees with a lateral direction of the endoscope image displayed on the endoscope image monitor.

A bending lock operation tab 105 and a bending lock lever 106 are rotatably operably mounted on the operation section 101 about the same rotation axis CX2 as two bending operation knobs 104a, 104b.

Various operation buttons 107 such as a freeze button, a recording button, a suction button, an air/water feeding button are also mounted on the operation section 101.

A universal cable 108 through which a signal cable, a light guide, various tubes and the like pass extends from one side surface of the operation section 101 through a bend preventing portion 108a.

The operation section 101 has a grasping portion 109 below two bending operation knobs 104a, 104b. The grasping portion 109 is a portion which allows a surgeon to grasp the operation section 101 with his left hand. A cross section of the grasping portion 109 orthogonal to the longitudinal axis C2 is formed in an approximately rectangular shape.

A treatment instrument insertion opening 110 is formed on a side surface at a position below the grasping portion 109.

The baby endoscope 1 is mounted on the grasping portion 109 of the operation section 101 of the mother endoscope 2 having the above-mentioned configuration.

As shown in FIG. 6 and FIG. 7, the baby endoscope 1 can be fixed to the mother endoscope 2 by winding the belt 16 around the grasping portion 109 of the mother endoscope 2 and by inserting the pin 17 into one of the plurality of holes 16a such that the belt 16 is tightly wound around an outer periphery of the grasping portion 109.

The grasping portion 109 of the operation section 101 has an approximately rectangular cross-sectional shape, and the operation section 11 of the baby endoscope 1 is mounted on the grasping portion 109 of the mother endoscope 2 such that a flat side surface portion of the operation section 11 of the baby endoscope 1 is brought into contact with a flat surface formed on an outer peripheral surface of the grasping portion 109.

More specifically, the pin 17 is inserted into the hole 16a so as to tightly press the grasping portion 109 against the operation section 11 of the baby endoscope 1 by the belt 16 in such a manner that the surface 11C which is a side surface of the operation section 11 is brought into contact with a portion of the side surface of the grasping portion 109 of the operation section 101 of the mother endoscope 2.

In other words, the exterior member 11a which forms the housing rotatably holds the rotary members about the predetermined rotation axis CX1, houses the rotary members 22a, 22b in the exterior member 11a, and has the surface 11C forming a contact surface which is directly brought into contact with a portion of an outer peripheral surface of the operation section 101 of the mother endoscope 2 on an outer peripheral portion.

In this embodiment, the surface 11C of the exterior member 11a is directly brought into contact with the portion of the outer peripheral portion of the operation section 101 of the mother endoscope 2. However, the surface 11C may be indirectly brought into contact with the portion of the outer peripheral portion of the operation section 101 by way of a flexible member.

The insertion section 12 of the baby endoscope 1 is inserted into the treatment instrument insertion channel from the treatment instrument insertion opening 110 of the mother endoscope 2 as indicated by a two-dot chain line IL in FIG. 7.

As shown in FIG. 6 and FIG. 7, when the operation section 11 of the baby endoscope 1 is mounted on the grasping portion 109 of the operation section 101, the longitudinal axis C1 of the operation section 11 and the longitudinal axis C2 of the operation section 101 become parallel to each other or become substantially parallel to each other, and the rotation axis CX2 of the bending operation knobs 104a, 104b and the rotation axis CX1 of the bending operation levers 14a, 14b become parallel to each other or become substantially parallel to each other.

When the baby endoscope 1 is mounted on the mother endoscope 2, when a surgeon grasps the grasping portion 109 of the operation section 101 of the mother endoscope 2 with his left hand LH, the surgeon can press the operation section 11 of the baby endoscope 1 with his left hand LH by making his middle finger or the like caught by the finger touching portion 15.

As shown in FIG. 1 and FIG. 6, two bending operation levers 14a, 14b are respectively mounted on the rotary members 22a, 22b, and two bending operation levers 14a, 14b are disposed within a width H such that two bending operation levers 14a, 14b do not go outside beyond the width H of the exterior member 11a in a direction of the rotation axis CX1 when the exterior member 11a which forms the housing is viewed in a direction orthogonal to the rotation axis CX1.

In other words, two bending operation levers 14a, 14b which form the operation members are respectively fixed to the rotary members 22a, 22b, and the whole two bending operation levers 14a, 14b are arranged to fall within the width H such that two bending operation levers 14a, 14b do not go outside beyond the width of the exterior member 11a in a direction of the rotation axis CX1 when the exterior member 11a is viewed in the direction orthogonal to the rotation axis CX1.

Further, when the exterior member 11a is fixed to the grasping portion 109 of the operation section 101 by the belt 16, two bending operation levers 14a, 14b are disposed on the surface 11A which makes an approximately 90 degrees with respect to the surface 11C which is a contact surface contacting with a portion of the outer peripheral surface of the operation section 101 and is parallel to the longitudinal axis C1.

With such a configuration, when the baby endoscope 1 is mounted on the mother endoscope 2, a thumb SF of a left hand LH of a surgeon which grasps the grasping portion 109 can operate not only the bending operation knobs 104a, 104b of the mother endoscope 2 but also the bending operation levers 14a, 14b of the baby endoscope 1.

Accordingly, when a surgeon inserts the insertion section 102 of the mother endoscope 2 into a subject, positions the distal end portion of the insertion section 12 of the baby endoscope 1 in the vicinity of a part to be observed or part to be treated, and operates the bending operation levers 14a, 14b of the insertion section 12 of the baby endoscope 1, the surgeon can operate the bending operation levers 14a, 14b of the baby endoscope 1 with his left hand LH without separating his right hand from the insertion section 12 of the baby endoscope 1 or from the insertion section 102 of the mother endoscope 2. As a result, the surgeon can smoothly perform an inspection or the like of the subject.

As has been described above, according to the above-mentioned embodiment, it is possible to realize a medical device having an operation section which is miniaturized so as to allow a surgeon to operate the medical device with his left hand which grasps the endoscope when the medical device is mounted on the endoscope.

Particularly, the rotary members 22a, 22b are disposed in the exterior member 11a of the operation section 11 of the baby endoscope 1 and hence, the bending operation levers 14a, 14b are disposed at the position close to a thumb SF of a left hand LH of a surgeon who grasps the operation section 101 of the mother endoscope 2. Accordingly, the surgeon can easily operate the bending operation levers 14a, 14b.

As a result, a surgeon can smoothly perform an inspection and a treatment using the mother-baby endoscope apparatus and hence, an inspection time period and a treatment time period can be shortened.

In the above-mentioned embodiment, the baby endoscope 1 includes two bending operation levers as the operation member. However, one bending operation lever, a plurality of, that is, three or more bending operation levers may be provided.

In the above-mentioned embodiment and modification, the operation member of the operation section 11 is formed of the bending operation member. However, when the baby endoscope has a zooming function, the operation member of the operation section 11 may be a member for a zooming operation, a member for locking bending or the like.

As a modification, in place of using bending operation levers, knurling may be applied to an outer peripheral surface of the rotary members 22a, 22b.

Figure 8:
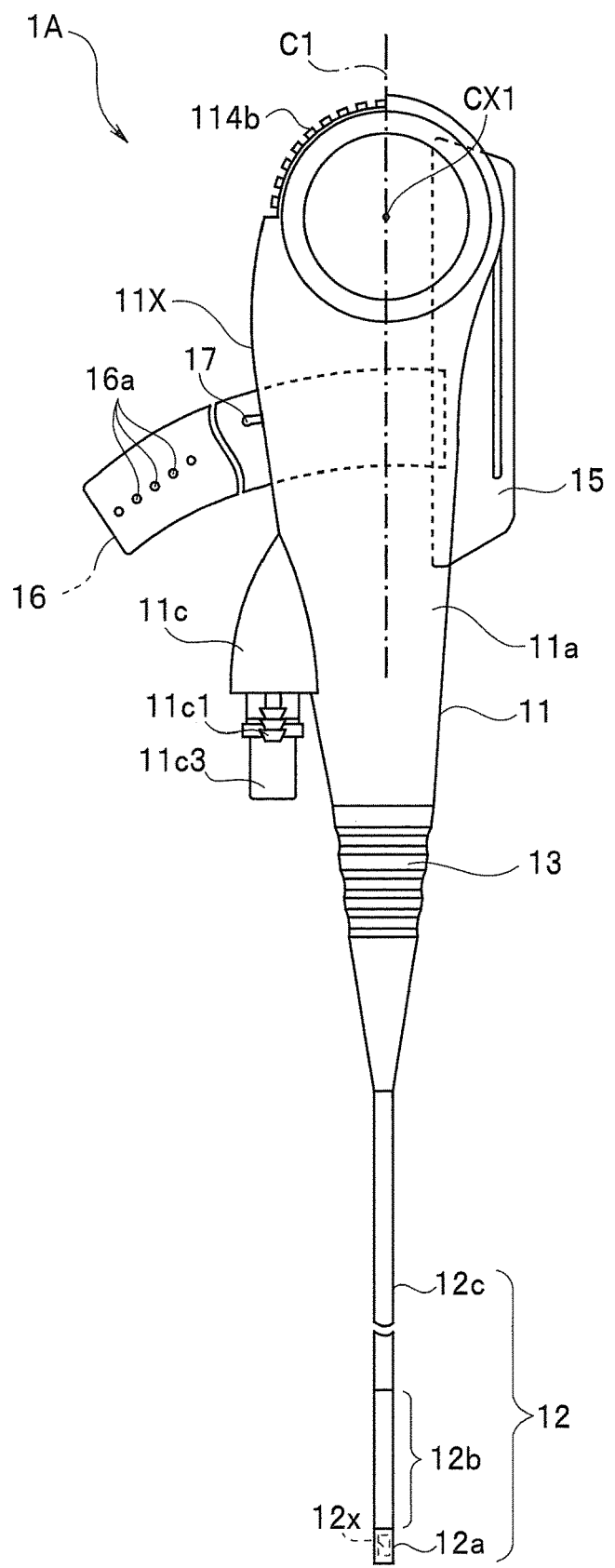
FIG. 8 is a side view of a baby endoscope 1A according to a modification of the embodiment of the present invention.
Figure 9:
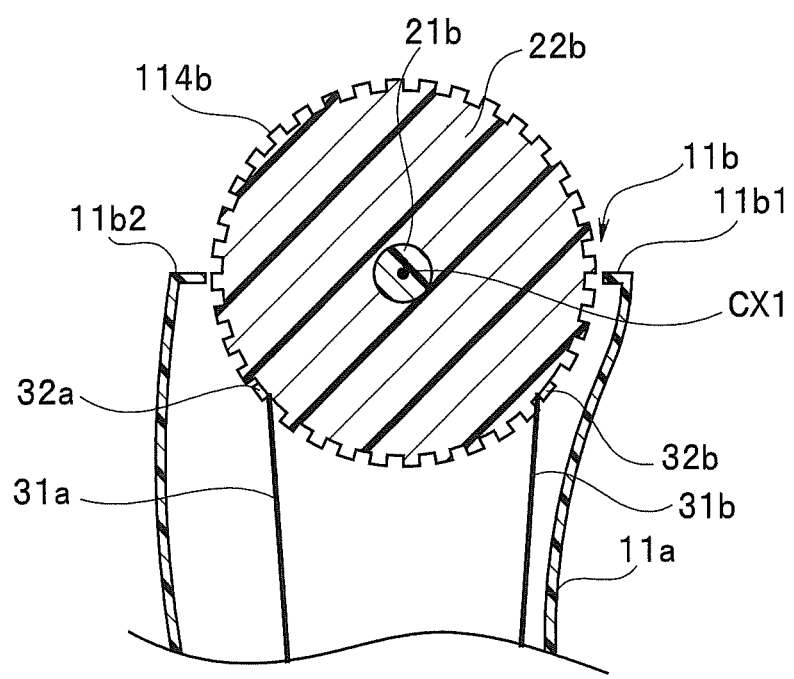
FIG. 9 is a cross-sectional view of an operation section 11X of the baby endoscope 1A according to the modification of the embodiment of the present invention taken along line IV-IV in FIG. 1.

FIG. 8 is a side view of a baby endoscope 1A according to the modification. FIG. 9 is a cross-sectional view of an operation section 11X of the baby endoscope 1A according to the modification taken along line IV-IV in FIG. 1.

In FIG. 8 and FIG. 9, components equal to the components of the baby endoscope 1 according to the above-mentioned embodiment are given the same symbols and the description of the components is omitted, and only components which differ from the corresponding components of the baby endoscope 1 of the above-mentioned embodiment are described.

In the modification, a knurling portion 114b which is formed of a plurality of concave and convex shapes is formed on outer peripheral portions of rotary members 22a, 22b. Although the knurling portion 114b formed on the rotary member 22b is shown in FIG. 8 and FIG. 9, the rotary member 22a also has substantially the same knurling portion. In other words, a knurling processed portion which forms an operation member is formed on outer peripheral portions of the rotary members 22a, 22b.

The knurling portion 114b is exposed from a surface of an exterior member 11a of an operation section 11 and hence, a surgeon can perform a bending operation using such a knurling portion. In other words, the exterior member 11a which forms the housing rotatably holds the rotary members 22a, 22b about a predetermined rotation axis CX1, and houses at least portions of the rotary members 22a, 22b in the exterior member 11a.

Further, in the above-mentioned embodiment and modification, the medical device which is used with the mother endoscope 2 is the baby endoscope 1. However, the above-mentioned embodiment and modification are applicable also to other medical devices such as a catheter.

The present invention is not limited to the above-mentioned embodiment, and various modifications and alterations can be made without departing from the gist of the present invention.

What is claimed is:

1. A medical device comprising:
   an insertion section having a bending portion which is bendable;
   a housing disposed on a proximal end side of the insertion section, the housing having a first surface and a second surface, the second surface being offset from the first surface; and
   an operation surface rotatably mounted on the second surface of the housing about a first rotation axis, the operation surface being configured to bend the bending portion,
   a fixing member configured to fix the first surface of the housing to another medical device;
   wherein the operation surface extends from an opening formed on the second surface,
   an entirety of the operation surface is disposed within a width of the housing in a direction of the first rotation axis when the housing is viewed in a direction orthogonal to the first rotation axis; and
   the first rotation axis intersects with the first surface.

2. The medical device according to claim 1, wherein the operation surface is provided in plurality.

3. The medical device according to claim 1, wherein the endoscope is a first endoscope and the medical device is a second endoscope different from the first endoscope.

4. The medical device according to claim 1, wherein the medical device is a catheter.

5. The medical device according to claim 1, wherein the operation surface is an operation lever, and a rotation range of the operation lever is restricted.

6. The medical device according to claim 1, wherein second surface is offset approximately 90 degrees relative to the first surface and is parallel to a longitudinal axis of the housing.

7. An endoscope system comprising:
   an endoscope; and
   a medical device fixed to an operation section of the endoscope, wherein the medical device comprising:
      an insertion section inserted into a treatment instrument insertion opening of the endoscope, the insertion section having a bending portion which is bendable;
      a housing disposed on a proximal end side of the insertion section, the housing having a first surface configured to be attached to a grasping portion of the endoscope; and
      an operation surface rotatably mounted on a second surface of the housing about a first rotation axis, the operation surface being configured to bend the bending portion, the operation surface extends from an opening formed on the second surface,
   wherein the first surface is formed such that the first rotation axis and a second rotation axis of a rotary member mounted on the operation section of the endoscope become parallel to each other or become substantially parallel to each other when the housing is mounted on the grasping portion of the endoscope,
   the second surface being offset from the first surface,
   an entirety of the operation surface is disposed within a width of the housing in a direction of the first rotation axis when the housing is viewed in a direction orthogonal to the first rotation axis; and
   the operation surface and the rotary member are aligned in a longitudinal axis direction of the housing.

8. The endoscope system according to claim 7, wherein the operation surface being disposed between the rotary member of the endoscope and the treatment instrument insertion opening when the first surface is attached to the grasping portion of the endoscope.

9. The endoscope system according to claim 7, wherein the grasping section includes a third surface on a side on which the operation knob is mounted, and the third surface faces the first surface when the first surface is attached to the grasping portion of the endoscope.

10. The endoscope system according to claim 7, wherein second surface is offset approximately 90 degrees relative to the first surface and is parallel to a longitudinal axis of the housing.

11. The endoscope system according to claim 7, wherein the operation surface is provided in plurality.

12. The endoscope system according to claim 7, wherein the endoscope is a first endoscope and the medical device is a second endoscope different from the first endoscope.

13. The endoscope system according to claim 7, wherein the medical device is a catheter.

14. The endoscope system e according to claim 7, wherein the operation surface is an operation lever, and a rotation range of the operation lever is restricted.

* * * * *